United States Patent [19]
Guillon et al.

[11] Patent Number: 4,492,686
[45] Date of Patent: Jan. 8, 1985

[54] COSMETIC MAKEUP CONTAINING COLORED PIGMENTS SALIFIED WITH AMINE FUNCTIONS

[75] Inventors: Michel Guillon, Bourg-la-Reine; Jean Mondet, Sevran; Christos Papantoniou, Montmorency; Claudine Vandenbossche, Aulnay-sous-Bois, all of France

[73] Assignee: Societe Anonyme dite: L'Oreal, Paris, France

[21] Appl. No.: 433,874

[22] Filed: Oct. 13, 1982

[30] Foreign Application Priority Data

Oct. 15, 1981 [FR] France ................. 81 19388

[51] Int. Cl.³ .............. A61K 7/04; A61K 7/021; A61K 31/00; A61K 47/00
[52] U.S. Cl. .......................... 424/61; 424/63; 424/64; 424/69; 424/168; 424/358; 424/DIG. 5; 525/351
[58] Field of Search ............ 424/61, 63, 64, 70, 424/DIG. 5, 168, 358, 69; 525/351

[56] References Cited

U.S. PATENT DOCUMENTS

| Re. 30,362 | 8/1980 | Gless, Jr. et al. | 525/355 |
| 3,974,271 | 8/1976 | Billington | 424/64 |
| 4,438,140 | 3/1984 | Guillon et al. | 424/61 |

FOREIGN PATENT DOCUMENTS

| 888488 | 10/1981 | Belgium. |
| 53-29940 | 3/1978 | Japan. |
| 1206542 | 9/1970 | United Kingdom. |
| 1347051 | 2/1974 | United Kingdom. |
| 1350284 | 4/1974 | United Kingdom. |
| 1356006 | 6/1974 | United Kingdom. |
| 1357342 | 6/1974 | United Kingdom. |
| 1427760 | 3/1976 | United Kingdom. |
| 2027437 | 2/1980 | United Kingdom. |
| 2073229 | 10/1981 | United Kingdom. |
| 2074584 | 11/1981 | United Kingdom. |

OTHER PUBLICATIONS

Patent Abstracts of Japan, vol. 2, No. 72.

Primary Examiner—Sidney Marantz
Assistant Examiner—Shawn P. Foley
Attorney, Agent, or Firm—Cushman, Darby & Cushman

[57] ABSTRACT

A cosmetic makeup composition contains in an appropriate cosmetically acceptable vehicle or carrier a colored pigment resulting from the salification reaction of a polymer having salified primary or secondary amine functions or quaternized tertiary amine functions and an acid dye, in free acid form or as a salt thereof, the acid dye being fixed on said polymer in an amount of at least 10 weight percent of the stoichiometric quantity.

The compositions include lip rouges, cheek rouges, foundation creams and nail enamels.

7 Claims, No Drawings

COSMETIC MAKEUP CONTAINING COLORED PIGMENTS SALIFIED WITH AMINE FUNCTIONS

The present invention relates to new cosmetic makeup compositions for the lips, the skin and the nails, such as lip rouge, check rouge, foundation creams and nail enamel, containing as the coloring substance a new class of colored pigments.

All makeup products contain, to a greater or lesser degree, a certain number of pigments which can be either mineral or organic.

These pigments, while coloring the compositions impart to the lips, the skin and the nails, a makeup effect more or less intense depending on the amount employed.

Numerous organic pigments, often known as "lakes", are currently employed in cosmetics for the purpose of imparting to the lips, the skin or the nails a makeup effect, these lakes being salts of calcium, barium, aluminum, zirconium and the like, of acid dyes such as halogen acid dyes, azoic acids or anthraquinoic acids.

Representative lakes include, in particular, those known under the names of D and C Red 21, D and C Orange 5, D and C Red 27, D and C Orange 10, D and C Red 3, D and C Red 7, D and C Red 2, D and C Red 4, D and C Red 8, D and C Red 33, D and C Yellow 5, D and C Yellow 6, D and C Green 5, D and C Yellow 10, D and C Green 3, D and C Blue 1, D and C Blue 2 and D and C Violet 1.

The shades provided by these different lakes are relatively limited and thus often fail to satisfy the varying tastes in fashion.

Moreover, these lakes, or at least a certain number of them, have a tendency to dye the surface of the skin, the mucous membrane or the keratin of the nail. This phenomenon is often referred to by cosmeticians as "grafting", that is to say, the capacity of a specified dye substance to more or less dye the lips, the skin or the nails.

Since current regulations are particularly strict as to the use of new lakes, research has been directed to certain derivatives of acid dyes of these lakes and in this regard mention is made of French Pat. No. 1,588,210 which describes in a lip rouge composition the use of salts of halogen acid dyes with certain amines, such as, diethanolamine, triethanolamine, 2-amino-2-methyl propanediol-1,3,monoisopropanolamine, morpholine and diglycolamine.

Nevertheless, such salts have not resolved the problems posed which are directed, on the one hand, to providing new shades and, on the other hand, to a satisfactory reduction in the "grafting" effect.

It has now been found that the various disadvantages of known pigments in cosmetic makeup compositions can be overcome by using in the makeup composition a new class of colored pigments. These new colored pigments result essentially from the salification reaction between an acid dye, or its salt, and a polymer having salified primary or secondary amine functions or quaternized tertiary amine functions. More particularly, this reaction can be considered as an ion exchange reaction between the dye and the polymer.

By using these new colored pigments or colored polymers it is now possible to provide makeup formulations, having shades or colors which can even be quite unordinary, and which considerably reduce or totally eliminate this "grafting" effect.

Additionally, it has been noted that there is essentially no change or alteration of the color of the compositions over a prolonged period of time, the color of the makeup product being practically identical to that of the color imparted to the skin or to the keratin of the nail.

The present invention thus relates to a cosmetic makeup composition and more particularly to a makeup composition for the lips, the face and the nails, said composition comprising in a cosmetically acceptable vehicle or carrier at least one colored pigment, the said colored pigment resulting from the salification reaction of a polymer having salified primary or secondary amine functions or quaternized tertiary amine functions, and an acid dye in the form of a free acid or a salt thereof, the said dye being fixed in an amount of at least 10 percent by weight of the stoichiometric quantity.

Preferably, the acid dye is fixed in an amount between 10 and 100%, the amount of dye fixed depending, however, on the intensity of the color that is desired.

Representative acid dyes capable of leading to the colored pigments or polymers for use in the compositions of the present invention include, in particular, those employed in the lakes, listed above, and more particularly the following:

(1) halogen acid dyes having the following formulas:

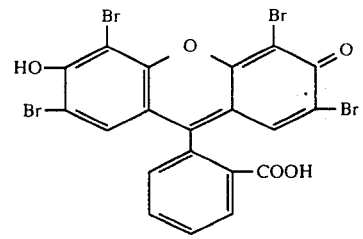

(I)
(D and C Red 21)

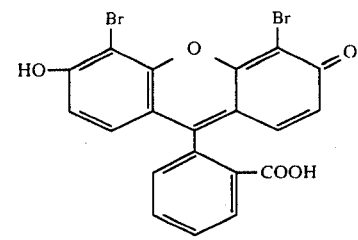

(II)
(D and C Orange 5)

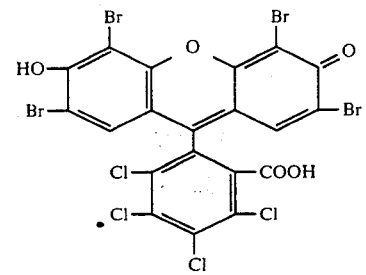

(III)
(D and C Red 27)

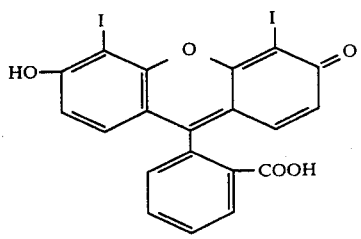

(IV)
(D and C Orange 10)

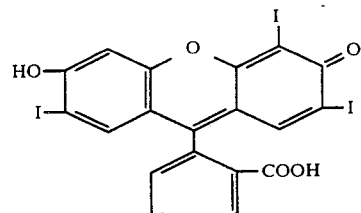

(V)
(D and C Red 3)

(2) Azo dyes having the following formulas:

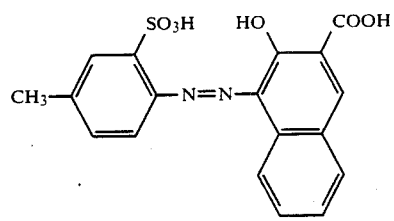

(VI)
(D and C Red 7)

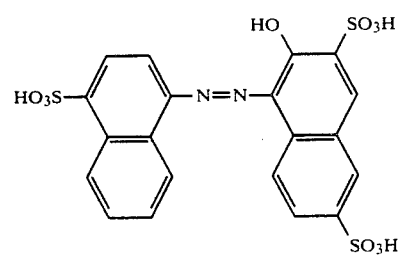

(VII)
(D and C Red 2)

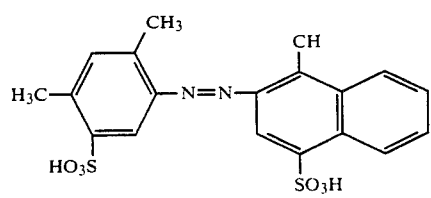

(VIII)
(D and C Red 4)

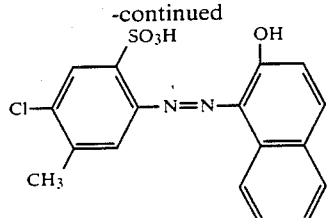

(IX)
(D and C Red 8)

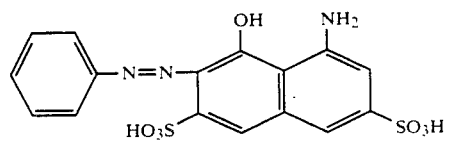

(X)
(D and C Red 33)

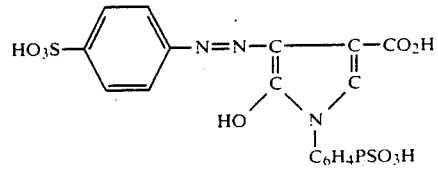

(XI)
(D and C Yellow 5)

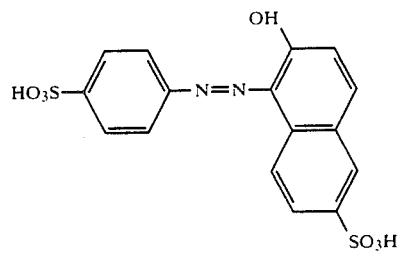

(XII)
(D and C Yellow 6)

(3) Anthraquinone dyes and principally the anthraquinone dye having the following formula

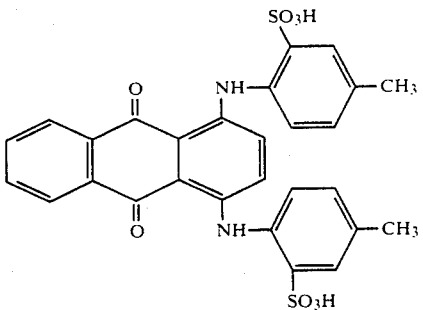

(XIII)
(D and C Green 5)

and (4) acid dyes having various structures among which include those of the lakes, D and C Yellow 10, D and C Green 3, D and C Blue 1, D and C Blue 2, and D and C Violet 1.

It will be noted that the acid dyes are not only those having at least a carboxylic acid function but also those having one or more sulfonic acid functions or acid dyes having both at least one carboxylic acid function and at least one sulfonic acid function.

The polymers having salified or quaternized amine functions can also have quite varied structures and can be provided either in the form of homopolymers or copolymers, of which the amine functions can be a part either of the principal chain of the polymer or be provided in the form of a lateral group, or even the amine functions can be included in a ring which itself serves as a link in the polymer chain.

Representative preferred polymers have salified primary or secondary amine functions or quaternized tertiary amine functions include, particularly:

(1) polyvinylamine salts, such as polyvinylamine hydrochloride having a molecular weight between 1,000 and 200,000, preferably between 2,000 and 150,000 (the molecular weight being determined by light diffusion or by gel permeation chromatography);

(2) homopolymers or copolymers having units of the formula

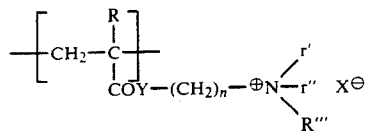

wherein
n is 2 or 3,
Y is O or NH,
R represents hydrogen or $CH_3$,
r', r" and r'" each independently represent alkyl having 1-6 carbon atoms, and
X is $Cl^-$, $Br^-$ or $CH_3SO_4^-$.

These polymers have a molecular weight between 1,000 and 200,000, preferably between 2,000 and 150,000 (the molecular weight being determined in accordance with the methods mentioned above).

Representative preferred homopolymers include the polymethacrylate of N,N-dimethyl-N-ethyl ammonium-2 ethyl bromide and the polyacrylamide of N,N-dimethyl-N-ethyl ammonium-3-propyl bromide. Representative copolymers include those having units derived from the polymerization of unsaturated monomers such as the methacrylates or acrylates of which the alkyl radical is linear or branched and contains from 1-18 carbon atoms;

(3) polymers, more often known as "ionenes", and principally those having units of the following formula:

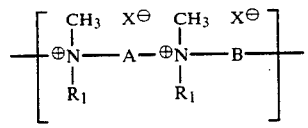

wherein
A and B, each independently, represent either a linear or branched alkylene radical having 2-18 carbon atoms, optionally substituted by hydroxy and/or interrupted by an oxygen atom, or a ureido group, or an o-, m- or p-xylylene group, $R_1$ represents alkyl having 1-18 carbon atoms, and
$X^\ominus$ is $Cl^\ominus$ or $Br^\ominus$.

These polymers have a molecular weight between 1,000 and 50,000, preferably between 2,000 and 30,000 (the molecular weight being determined in accordance with the methods mentioned above).

Such polymers are more particularly described in French Pat. Nos. 75.15161 and 78.17899.

Representative preferred ionenes for use in the present invention include poly-N,N,N',N'-tetramethyl, N-dimethylene p-xylylene diammonium dihalide of the formula

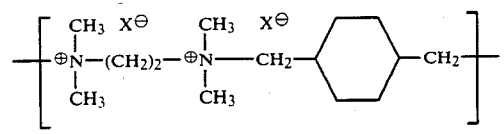

and in particular, poly-N,N,N',N'-tetramethyl N-dimethylene p-xylylene diammonium dibromide;

(4) cyclic homopolymers or copolymers having units of the formula:

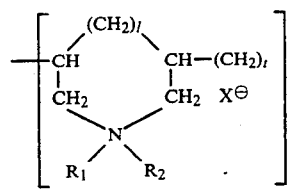

wherein
l=0 or 1,
if l=0, t=1 and if l=1, t=0,
$R_1$ and $R_2$, each independently, represent alkyl having 1-18 carbon atoms, and
X is $Cl^\ominus$ or $Br^\ominus$.

These polymers have a molecular weight between 1,000 and 50,000, preferably between 2,000 and 30,000, (the molecular weight being determined in accordance with the methods mentioned above).

Representative preferred homopolymer includes that obtained starting with N,N-dimethyl N,N-diallyl ammonium chloride ($R_1=R_2=CH_3$ and $X^\ominus=Cl^\ominus$).

When the polymers are provided in the form of copolymers, the other units result from the use, during polymerization, of unsaturated monomers such as acrylamide, N-vinyl pyrrolidone, vinylesters, acrylic esters or methacrylic esters and the like.

Representative homopolymers and copolymers of this type include, in particular, those described in French Pat. Nos. 71.06387, 73.23970, 77.15088 as well as in U.S. Pat. No. 3,862,091 and principally those commercialized under the tradename MERQUAT.

The colored pigments or colored polymers used in the compositions of the present invention are obtained by reacting, with agitation, in an aqueous medium, preferably water, a solution of an acid dye or a salt thereof and a solution or dispersion of a polymer having salified or quaternized amine functions, the reaction preferably being carried out at ambient temperature for a sufficient period of time, in the order of 15 minutes to 5 hours, so that the dye is fixed on the basic sites of the polymer.

To accelerate the reaction it is possible to heat the reaction mixture to a temperature of, for example, about 30° to 60° C.

After the reaction, the resulting product is filtered and washed with water until the last wash waters are colorless and free from residual acidity.

The resulting colored pigment is dried and before use in a cosmetic composition, it can be previously ground to an appropriate granulometry, preferably lower than about 250 microns.

The analyses carried out on the colored polymers thus obtained have shown that the fixation of the dye is effected in excellent conditions, the percentage of the non-fixed dye being lower than about 1%.

The cosmetic makeup compositions according to the present invention can be provided in the form of sticks, pastes, emulsions, suspensions, dispersions, powders or solutions and constitute lip rouges, mascaras, lip gloss, cheek rouge, eyelid shadow, foundation creams, eye-liners, powders or even nail enamels.

In the compositions according to the present invention the amount of colored polymer is generally between 0.1 and 20 weight percent based on the total weight of the composition. The concentration, however, depends upon the intensity of the coloration that one desires to impart to the compositions.

According to the present invention the colored polymer can be combined with organic or mineral pigments and principally with lakes such as those currently employed and listed above.

The mineral pigments are, generally, iron oxides (red, brown, black and yellow), chrome oxides, ultramarines (polysulfides of amino silicates), titanium dioxide, manganese pyrophosphate and Prussian blue (ferric ferrocyanide). These different compounds, alone or in admixture, are generally employed in an amount between 0.1 and 40 weight percent, based on the total weight of the cosmetic composition.

Moreover, these compositions can also contain nacreous agents such as bismuth oxychloride, titanium mica, and guanine crystals.

When the compositions are provided in the form of sticks and principally lip rouges, eyelid shadow, cheek rouge and foundation creams, a significant portion of these compositions comprises a fatty body which can be constituted from one or more waxes. Representative waxes include, for example, ozokerite, lanolin, lanolin alcohol, hydrogenated lanolin, acetylated lanolin, lanolin wax, beeswax, Candellila wax, microcrystalline wax, Carnauba wax, cetyl alcohol, stearyl alcohol, cocoa butter, lanolin fatty acids, petrolatum, vaselines, mono-, di- and tri-glycerides solid at 25° C., fatty esters solid at 25° C., silicone waxes such as methyloctadecane-oxy polysiloxane and poly (dimethylsiloxy) stearoxysiloxane, stearic monoethanolamide, colophony and its derivatives such as glycol or glycerol abietates, hydrogenated oils solid at 25° C., sucroglycerides and the oleates, myristates, lanolates, stearates and dihydroxy stearates of calcium, magnesium, zirconium and aluminum.

The fatty body can also be constituted from a mixture of at least one wax and from at least one oil. Representative oils include, for example, paraffin oil, Purcellin oil, perhydrosqualene, sweet almond oil, avocado oil, calophyllum oil, ricin oil, sesame oil, jojoba oil, mineral oils having a boiling point between 310° and 410° C., silicone oils such as dimethyl polysiloxanes, linoleic alcohol, linolenic alcohol, oleic alcohol, oil of cereal germ such as oil of wheat germ, isopropyl lanolate, isopropyl palmitate, isopropyl myristate, butyl myristate, cetyl myristate, hexadecyl stearate, butyl stearate, decyl stearate, acetyl glycerides, the octanoates and decanoates of alcohols and polyalcohols such as those of glycol and glycerol, the ricinoleates of alcohols and polyalcohols such as that of cetyl alcohol, isostearyl alcohol, isocetyl lanolate, isopropyl adipate, hexyl laurate and octyldodecanol.

Generally, the fatty body in these compositions, in the form of a stick, represents up to 99.9% by weight of the total weight of the composition.

These compositions can also contain other components such as, for example, glycols, polyethyleneglycols, polypropylene glycols, monoalkanolamides, non-colored polymers, mineral or organic charges, preservatives, U.V. filters or other conventional cosmetic additives.

These compositions, in the form of a stick, are preferably anhydrous; however, in certain instances, they can contain a certain amount of water not exceeding, generally, 40 weight percent relative to the total weight of the cosmetic composition.

When the cosmetic compositions according to the present invention are provided in the form of a semi-solid, i.e., in the form of a paste or cream, they can be either anhydrous or aqueous and constitute mascaras, eye-liners, foundation creams, cheek rouge, eye shadow, lip rouge or anti-circle preparations and the like.

When these pastes or creams are, on the other hand, in an aqueous or liquid form, they are generally emulsions of the water-in-oil or oil-in-water type wherein the oil phase represents from 1 to 98.8 percent by weight, the water phase from 1 to 98.8 percent and the emulsifying agent from 0.1 to 30 weight percent.

These compositions can also contain other conventional adjuvants such as perfumes, anti-oxidants, preservatives, gelling agents, U.V. filters, dyes, pigments, nacreous agents, colorless polymers and mineral or organic charges.

When the compositions of the present invention are provided in the form of a powder, they are essentially prepared from a mineral or organic charge such as talc, kaolin, starches, polyethylene powders or polyamide powders, as well as additives such as binding agents, dyes and the like.

Such compositions can also contain various conventional cosmetic adjuvants such as perfumes, antioxidants and preservatives.

The compositions according to the present invention, when they are provided in the form of a nail enamel, are essentially produced from nitrocellulose and a natural or synthetic polymer in solution in a solvent system, this solution containing, optionally, other additives such as pigments and/or nacreous agents.

According to this embodiment of the invention, the colored polymer is present in an amount between 0.1 and 5 percent by weight.

The following non-limiting examples are given to illustrate the present invention and include several examples showing the preparation of the colored pigments as well as several examples illustrating cosmetic compositions containing the colored pigments or polymers.

PREPARATION OF COLORED POLYMERS

Example 1

Into a solution containing 1 g of the sodium salt of the dye, D and C Red 33 and 20 g of water there is slowly added, with vigorous agitation, a solution containing 0.5 g of polyvinylamine hydrochloride and 4.5 g of water.

Agitation of this mixture is continued for 1 hour 30 minutes out of contact with light. The reaction mixture is then filtered on fritted glass and the recovered colored polymer is washed several times with water until the wash waters are colorless.

After drying there is thus obtained the desired colored polymer in the form of its salt in a yield of 65%.

In accordance with the same operating procedures described in Example 1, the following colored polymer salts have been prepared, as outlined in Examples 2–9 which are set forth in the following Table.

TABLE

| Example | Dye | Polymer | Yield, % |
|---|---|---|---|
| 2 | D and C Yellow 10 (free acid) | homopolymer of poly N,N, N', N'—tetramethyl N—dimethylene p-xylylene diammonium dibromide | 55 |
| 3 | D and C Blue 1 (sodium salt) | homopolymer of poly N,N, N', N'—tetramethyl N—dimethylene p-xylylene diammonium dibromide | 90 |
| 4 | D and C Green 5 (sodium salt) | MERQUAT 100* | 45 |
| 5 | D and C Yellow 5 (sodium salt) | Polyvinylamine hydrochloride | 55 |
| 6 | D and C Yellow 6 (sodium salt) | Polyvinylamine hydrochloride | 55 |
| 7 | D and C Yellow 5 (sodium salt) | MERQUAT 100 | 40 |
| 8** | D and C Red 4 (sodium salt) | MERQUAT 100 | 60 |
| 9 | D and C Yellow 5 (sodium salt) | homopolymer of the polymethacrylate of N,N—dimethyl-N—ethyl ammonium-2 ethyl bromide | 45 |

*Merquat 100 (sold by Merck) in the commercial name of the homopolymer obtained starting with N,N—dimethyl-N,N—diallylammonium bromide
**The precipitate is washed with water at 50° C., then with a 50/50 acetone/water mixture.

EXAMPLES OF COMPOSITIONS

Example A

In accordance with the present invention a lip rouge is prepared by admixing the following components:

| | |
|---|---|
| Microcrystalline wax | 11 g |
| Vinyl polylaurate | 20 g |
| 1-docosanoyl (2-ethyl)-3-hexyloxy-2-propanol | 20 g |
| Liquid lanolin | 9 g |
| Ricin oil | 8 g |
| Sesame oil | 10 g |
| Acetoglyceride | 9 g |
| Petrolatum oil | 5 g |
| Oleyl alcohol | 5 g |
| Butylhydroxytoluene | 0.2 g |
| Polyethylene wax | 2.8 g |
| Black iron oxide | 0.2 g |
| Titanium oxide | 1.1 g |
| Colored polymer of Ex. 2 | 2.4 g |
| Colored polymer of Ex. 1 | 6 g |
| Perfume | 0.8 g |

Example B

A cheek rough is prepared, in the form of a compact powder, by admixing the following components:

| | |
|---|---|
| Talc | 41.64 g |
| Starch | 10 g |
| Zinc stearate | 2 g |
| Bismuth oxychloride | 10 g |
| Ricin oil | 0.7 g |
| Petrolatum oil | 3.5 g |
| Oleyl alcohol | 0.6 g |
| Phytosterol | 0.3 g |
| Oleates of polypeptides | 0.3 g |
| Butyl hydroxyanisole | 0.01 g |
| Magnesium carbonate | 0.55 g |
| Manganese violet | 7 g |
| Iron oxide | 2 g |
| Titanium mica | 20 g |
| Colored polymer of Ex. 1 | 0.5 g |
| Perfume | 0.4 g |
| Isopropyl myristate | 0.5 g |

EXAMPLE C

In accordance with the present invention a nail enamel is prepared by admixing the following components:

| | |
|---|---|
| Nitrocellulose, 0.5 sec. | 12 g |
| Aryl sulfonamide formaldehyde copolymer | 8 g |
| Camphor | 2 g |
| Butyl phthalate | 4 g |
| Ethyl acetate | 10 g |
| Toluene | 20 g |
| Ethyl alcohol | 3 g |
| Butyl alcohol | 3 g |
| Butyl acetate | 38 g |
| Bentone 27 | 1 g |
| Phosphoric acid | 0.01 g |
| Titanium oxide | 0.5 g |
| Brown iron oxide | 0.3 g |
| Colored polymer of Ex. 3 | 8 g |

What is claimed is:

1. In a cosmetic makeup composition for application to the lips, skin or nails comprising a cosmetically acceptable vehicle for the lips, skin or nails and a colored pigment, wherein the improvement comprises, as said colored pigment, 0.1 to 20 weight percent of a colored pigment resulting from the salification reaction in an aqueous medium of an azo dye selected from the group consisting of D and C Red 7, D and C Red 8, D and C Red 33, D and C Yellow 5, D and C Yellow 6, D and C Red 2 and D and C Red 4, with polyvinylamine hydrochloride, said colored pigment having a molecular weight between 1,000 and 200,000, said dye being attached to polyvinylamine hydrochloride by said salification reaction in an amount of at least 10 weight percent of the stoichiometric quantity.

2. The cosmetic makeup composition of claim 1 wherein the azo dye is attached to said polyvinylamine hydrochloride via the salification reaction in an amount between 10 and 100 percent of the stoichiometric quantity.

3. The cosmetic makeup composition of claim 1 which also contains a mineral pigment present in an amount ranging from 0.1 to 40 percent by weight based on the total weight of said composition said mineral pigment being selected from the group consisting of iron oxide, chrome oxide, ultramarine, titanium dioxide, manganese pyrophosphate or Prussian blue or a mixture thereof.

4. The cosmetic makeup composition of claim 1 wherein said cosmetically acceptable vehicle is a fatty body comprising a cosmetically acceptable wax or a mixture of a cosmetically acceptable wax and a cosmetically acceptable oil, said makeup composition being in the form of a stick.

5. The cosmetic makeup composition of claim 1 which also contains an effective amount of a nacreous agent selected from bismuth oxychloride, titanium mica or guanine crystals.

6. The cosmetic makeup composition of claim 1 wherein said cosmetically acceptable vehicle is an emulsion consisting of an oil phase, an aqueous phase and an emulsifying agent, wherein based on the total weight of said composition, the oil phase represents from 1 to 98.8 weight percent thereof, the water phase represents from 1 to 98.8 weight percent thereof and the emulsifying agent represents from 0.1 to 30 weight percent thereof.

7. The cosmetic makeup composition of claim 1 wherein said cosmetically acceptable vehicle is talc, kaolin, starch, polyethylene powder or polyamide powder, said makeup composition being in the form of a compact or loose powder.

* * * * *